United States Patent
Gilbert et al.

(12)

(10) Patent No.: US 10,934,596 B2
(45) Date of Patent: Mar. 2, 2021

(54) AUTOMATED MICROBIAL DETECTION AND QUANTIFICATION

(71) Applicant: UCHICAGO ARGONNE, LLC, Chicago, IL (US)

(72) Inventors: Jack Gilbert, Naperville, IL (US); Charles Catlett, Lemont, IL (US); Peter Beckman, Lemont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 295 days.

(21) Appl. No.: 15/949,516

(22) Filed: Apr. 10, 2018

(65) Prior Publication Data

US 2018/0305772 A1    Oct. 25, 2018

Related U.S. Application Data

(60) Provisional application No. 62/488,672, filed on Apr. 21, 2017.

(51) Int. Cl.

| | |
|---|---|
| *C12P 19/34* | (2006.01) |
| *C12Q 1/6888* | (2018.01) |
| *C12Q 1/6825* | (2018.01) |
| *C12Q 1/689* | (2018.01) |
| *C12Q 1/70* | (2006.01) |
| *B01L 3/00* | (2006.01) |
| *G01N 27/02* | (2006.01) |
| *G01N 21/64* | (2006.01) |
| *C12Q 1/6844* | (2018.01) |
| *G01N 15/14* | (2006.01) |
| *G01N 1/22* | (2006.01) |
| *G01N 15/00* | (2006.01) |

(52) U.S. Cl.
CPC ...... *C12Q 1/6888* (2013.01); *B01L 3/502715* (2013.01); *C12Q 1/689* (2013.01); *C12Q 1/6825* (2013.01); *C12Q 1/6844* (2013.01); *C12Q 1/701* (2013.01); *G01N 1/2273* (2013.01); *G01N 15/1459* (2013.01); *G01N 15/1484* (2013.01); *G01N 21/6428* (2013.01); *G01N 27/021* (2013.01); *B01L 2200/0647* (2013.01); *B01L 2200/0652* (2013.01); *B01L 2200/16* (2013.01); *B01L 2300/0636* (2013.01); *B01L 2300/0645* (2013.01); *B01L 2300/0672* (2013.01); *B01L 2400/0415* (2013.01); *G01N 2001/2223* (2013.01); *G01N 2015/0046* (2013.01); *G01N 2015/0065* (2013.01); *G01N 2021/6439* (2013.01)

(58) Field of Classification Search
None
See application file for complete search history.

(56) References Cited

U.S. PATENT DOCUMENTS

| 8,431,390 B2 | 4/2013 | Jovanovich et al. | |
|---|---|---|---|
| 2004/0156753 A1* | 8/2004 | Roitman | B01J 19/0093 |
| | | | 422/504 |
| 2006/0159594 A1* | 7/2006 | Parker | F24F 3/16 |
| | | | 422/121 |
| 2007/0029477 A1* | 2/2007 | Miller | G01N 30/7206 |
| | | | 250/290 |
| 2012/0295269 A1* | 11/2012 | Pourahmadi | B01D 15/00 |
| | | | 435/6.12 |

OTHER PUBLICATIONS

Esfandyarpouremail, et al., "Label-free electronic probing of nucleic acids and proteins at the nanoscale using the nanoneedle biosensor," Biomicrofluidics 7, 044114, 13 pages (2013).

Esfandyarpouremail, et al., "Nanoelectronic three-dimensional (3D) nanotip sensing array for real-time, sensitive, label-free sequence specific detection of nucleic acids," Biomedical Microdevices 18(7), 19 pages (2016).

Hardenbol, et al., "Highly multiplexed molecular inversion probe genotyping: Over 10,000 targeted SNPs genotyped in a single tube assay," Genome Research 15, pp. 269-275 (2005).

Hardenbol, et al., "Multiplexed genotyping with sequence-tagged molecular inversion probes," Nature Biotechnology 21, pp. 673-678 (2003).

Hyman, et al., "Molecular probe technology detects bacteria without culture," BMC Microbiology 12(29), 10 pages (2012).

Hyman, et al., "Multiplex Identification of Microbes," Applied and Environmental Biology 76(1), pp. 3904-3910 (2010).

Krishnakumar, et al., "A comprehensive assay for targeted multiplex amplification of human DNA sequences," Proceedings of the National Academy of Sciences 105(27), pp. 9296-9301 (2008).

Smith, et al al., "A method for high-throughput production of sequence-verified DNA libraries and strain collections," Molecular Systems Biology 13(2), 913, 15 pages (2017).

Xu, et al., "Targeted and highly multiplexed detection of microorganisms by employing an ensemble of molecular probes," Applied and Environmental Microbiology 80, pp. 4153-4161 (2014).

* cited by examiner

*Primary Examiner* — Kenneth R Horlick
(74) *Attorney, Agent, or Firm* — Foley & Lardner LLP

(57) ABSTRACT

A method for automated microbial detection includes collecting air particles into a solid-state sampler, the air particles including microbes, charging the air particles using a plasma field generated by propulsion electrodes, focusing the charged air particles toward a sample well of a microfluidic testing cartridge, tagging the charged air particles with a fluorescence marker, and detecting a quantity of the microbes using a fluorescence detector.

11 Claims, 3 Drawing Sheets

AUTOMATED MICROBIAL DETECTION AND QUANTIFICATION

CROSS-REFERENCE TO RELATED APPLICATION

This application claims priority to and the benefit of U.S. Provisional Patent Application No. 62/488,672, filed on Apr. 21, 2017, the content of which is fully incorporated by reference herein in its entirety.

STATEMENT OF GOVERNMENT INTEREST

The United States Government claims certain rights in this invention pursuant to Contract No. DE-AC02-06CH11357 between the U.S. Department of Energy and U. Chicago Argonne, LLC, as operator of Argonne National Laboratory.

FIELD OF THE INVENTION

The present invention generally relates to automated microbial detection and quantification. Specifically, the present invention relates to automated sampling devices and methods for repeated characterization and remote data transfer of urban air and water microbiome.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Environmental infectious disease transmission is a central problem for high-density urban environments where diverse bacteria, protists and viruses are capable of migrating rapidly by air and water, colonizing new niches, transferring between animal and human hosts, developing new functional capabilities, and transforming urban metabolites.

Conventionally, urban development has focused on constructing operational infrastructure as the preferred means for protecting public health, supporting industry, reducing traffic congestion, and using resources in efficient and equitable ways. Urban planning has typically concentrated on top-down interventions involving centrally controlled infrastructure. While these efforts were critical for the growth of industrial cities, they are not sustainable. Current approaches (i.e. the "smart city" approach) still primarily view cities as mechanistic systems composed of discrete components to be optimized individually. Thus, a more holistic, systemic approach is necessary to facilitate greater appreciation of the elements that can be manipulated to achieve optimization.

Moreover, only a few studies have investigated the diversity and dynamics of microbial assemblages in the air, water, built environment, and soil systems of complex urban environments because of high financial and time commitments in manually sampling microbial organisms and an inability to obtain enough biomass to determine detection limits in existing technology. Existing tools for characterizing microbiomes are expensive and cumbersome apparatuses that require extensive personnel and time and which cannot be remotely deployed or wirelessly transmit data without expensive robotization. After microbial samples are collected, additional processing steps are required using separate equipment for labeling with a fluorescence marker. These processing steps are expensive and time consuming.

A need exists for improved technology, including an automated microbial detection and quantification system and a method for automated microbial detection and quantification.

SUMMARY

In one embodiment, a method for automated microbial detection includes collecting air particles into a solid-state sampler, the air particles including microbes, charging the air particles using a plasma field generated by propulsion electrodes, focusing the charged air particles toward a sample well of a microfluidic testing cartridge, tagging the charged air particles with a fluorescence marker, and detecting a quantity of the microbes using a fluorescence detector.

In one embodiment, the method for automated microbial detection also includes transmitting a signal of the fluorescence detector to a remote storage and analysis device, discarding the microfluidic testing cartridge, and loading an unused microfluidic testing cartridge. In one embodiment, the microbes comprise at least one of bacteria, archaea, fungi, viruses, or a combination thereof. In one embodiment, the solid-state sampler is an electro-kinetic ion focuser.

In one embodiment, the step of tagging the charged air particles includes puncturing a liquid cartridge comprising cell-lysis chemicals with an impaling structure embedded in the microfluidic testing cartridge to release the cell-lysis chemicals, flowing the released cell-lysis chemicals into the sample well to mix with the charged air particles and form a blend, flowing the blend into a mixing chamber of the microfluidic testing cartridge to re-suspend the charged particles in the cell-lysis chemicals, and distributing the blend into at least one assay chamber of the microfluidic testing cartridge. In one embodiment, the step of distributing the blend into at least one assay chamber includes activating pre-existing DNA polymerase, genotype-specific DNA oligomer primers for specific microbes, and fluorescent marker in each assay chamber, heating each assay chamber to enable isothermal DNA amplification, and binding the amplified DNA with the fluorescent marker. In one embodiment, the DNA polymerase is a Phi29 rolling circle DNA polymerase. In one embodiment, the cell-lysis chemicals comprise a lysis buffer, cellular lysate, and at least one detergent.

In another embodiment, an automated microbial detection system includes a solid-state sampler for collecting air particles, the air particles including microbes, propulsion electrodes for generating a plasma field to charge the collected air particles, a microfluidic testing cartridge for tagging the charged air particles with a fluorescence marker, and a fluorescence detector for detecting a quantity of the tagged charged air particles. In one embodiment, the solid-state sampler is an electro-kinetic ion focuser. In one embodiment, the propulsion electrodes are incorporated within the solid-state sampler. In one embodiment, the microbes comprise at least one of bacteria, archaea, fungi, viruses, or a combination thereof.

In one embodiment, the microfluidic testing cartridge includes a liquid cartridge including cell-lysis chemicals, an impaling structure embedded in a well of the microfluidic testing cartridge, a sample well for receiving the charged air particles from the solid-state sampler and cell-lysis chemicals from one of the liquid cartridge or the well, and a plurality of assay chambers for segregating the charged air particles based on the class of microbe. In one embodiment, the fluorescence detector is a nanoneedle biosensor including a plurality of conductive layers separated by at least one insulating layer, a detecting nano-sized gap separating at least one pair of sensing electrodes located at a tip of the nanoneedle biosensor, the tip being conjugated to detect oligonucleotides by surface functionalization, a microfluidic channel for accepting the tagged charged air particles, such that the tip measures changes in impedance across the sensing electrodes based on the surface functionalization of the detected oligonucleotides.

In another embodiment, a microfluidic testing cartridge includes a liquid cartridge including cell-lysis chemicals, an impaling structure embedded in a well of the microfluidic testing cartridge, a sample well for receiving charged air particles from a solid-state sampler and cell-lysis chemicals from one of the liquid cartridge or the well, the charged air particles including microbes, and a plurality of assay chambers for segregating the charged air particles based on class of the microbes. In one embodiment, the microbes comprise at least one of bacteria, archaea, fungi, viruses, or a combination thereof. In another embodiment, a nanoneedle biosensor includes a plurality of conductive layers separated by at least one insulating layer, a detecting nano-sized gap separating at least one pair of sensing electrodes located at a tip of the nanoneedle biosensor, the tip being conjugated to detect oligonucleotides by surface functionalization, a microfluidic channel for accepting the surface-functionalized oligonucleotides, such that the tip measures changes in impedance across the sensing electrodes based on the surface functionalization of the detected oligonucleotides.

In another embodiment, a method of tagging charged particles includes puncturing a liquid cartridge including cell-lysis chemicals with an impaling structure to release the cell-lysis chemicals, mixing the released cell-lysis chemicals with charged particles to form a blend, contacting the blend with a mixture comprising DNA polymerase, genotype-specific DNA oligomer primers for specific microbes, and fluorescent marker to form a system, heating the system to enable isothermal DNA amplification, and binding the amplified DNA with the fluorescent marker, such that the charged particles are suspended in the cell-lysis chemicals.

In one embodiment, the DNA polymerase is a Phi29 rolling circle DNA polymerase. In one embodiment, the cell-lysis chemicals comprise a lysis buffer, cellular lysate, and at least one detergent.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which.

DETAILED DESCRIPTION

Figure 1:
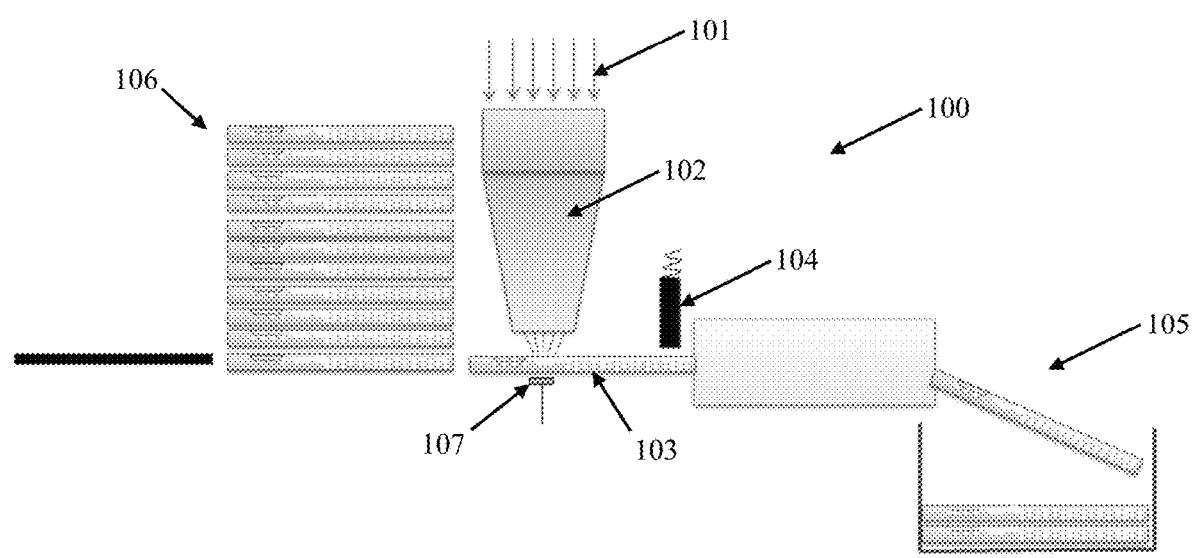
FIG. 1 illustrates an automated microbial detection system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

The present disclosure describes an automated sampling device and method for repeated characterization and remote data transfer of urban air and water microbiome. The automated sampling and microbial community characterization device may be adapted to both air and water systems, deployed in low accessibility locations, and remotely transfer microbial community profiles for continuous data acquisition. FIG. 1 illustrates an exemplary automated microbial detection system 100. In one embodiment, the automated microbial detection system comprises a solid-state sampler 102 for collection of air particles 101, with the air particles 101 including microbes. In one embodiment, the microbes may include at least one of bacteria, archaea, fungi, viruses, or a combination thereof. In one embodiment, the solid-state sampler 102 may be an electro-kinetic ion focuser. In an alternate embodiment, the solid-state sampler 102 may be adapted for collection of water samples.

As described in greater detail below, the solid-state sampler 102 charges the air particles 101 as they pass through the solid-state sampler 102 and the resulting ions are directed toward a microfluidic testing cartridge 103 positioned between the solid-state sampler 102 and a capture electrode 107. In one embodiment, the solid-state sampler 102 is capable of particle collection at rates of at least 150 L/min and utilizes electro-kinetic propulsion principles whereby large volumes of air are propelled through the solid-state sampler 102 with no moving parts as electrically-charged aerosol particles are focused onto the capture electrode 107. The charged air particles are then tagged with a fluorescence marker according to the description of FIG. 3 after segregating the charged air particles into a plurality of assay chambers of the microfluidic testing cartridge 103 based on the type of microbe (see below). Analysis is conducted with a fluorescence detector 104 which transmits a wireless signal to a remote storage and analysis device, the signal containing data on the quantity of each type of microbe from each individual assay chamber. In one embodiment, an electrical impedance detector based on oligonucleotide probe binding technology may also be used. The used microfluidic testing cartridge 105 may be subsequently discarded or analyzed further and an unused testing cartridge 103 may be automatically positioned in-between the solid-state sampler 102 and capture electrode 107 from a cartridge stack 106. In one embodiment, the cartridge stack 106 may be configured for holding at least one hundred microfluidic testing cartridges.

Figure 2:
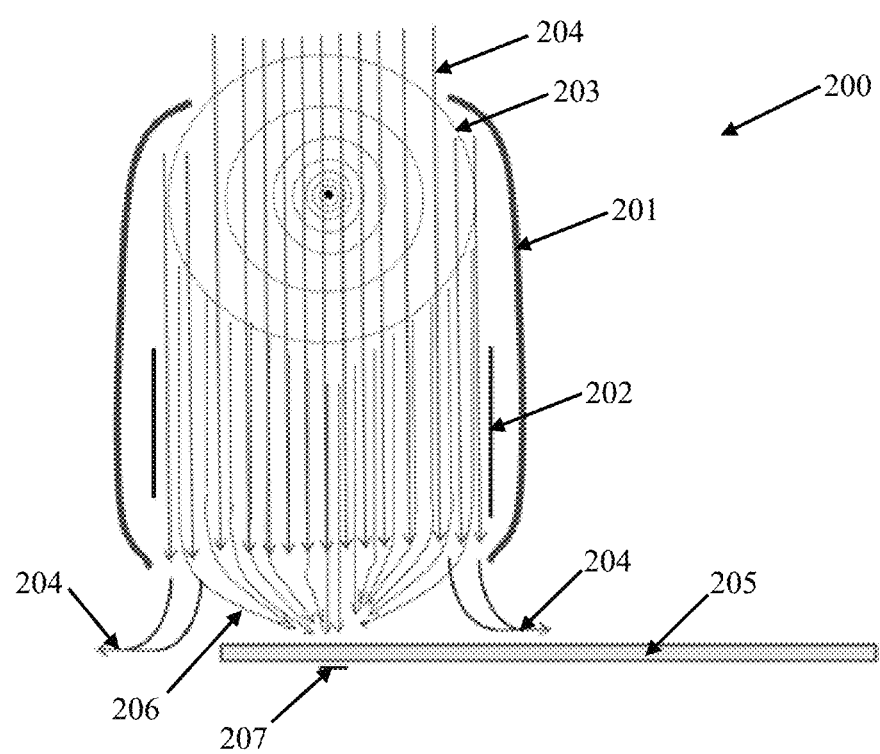
FIG. 2 illustrates a cross-section depiction of a solid-state sampler according to one embodiment of the automated microbial detection system.

FIG. 2 illustrates a cross-section depiction of a solid-state air sampler 200 according to one embodiment. The solid-state air sampler 200 includes a housing 201 within which is incorporated at least one pair of propulsion electrodes 202. The propulsion electrodes 202 are configured to generate a plasma field 203 through which a stream of air particles 204 is flown. The stream of air particles 204 may also include at least one type of microbe selected from bacteria, archaea, fungi, viruses, or combinations thereof. As the stream of air particles 204 flow through the solid-state air sampler 200 and between the propulsion electrodes 202, the air particles 204 attain a charge, resulting in a stream of ions (i.e. charged particles) 206 which are directed toward a capture electrode 207 situated below an intervening microfluidic testing cartridge 205. As a result, the charged particles 206 are collected in a sample well of the microfluidic testing cartridge 205.

Figure 3:
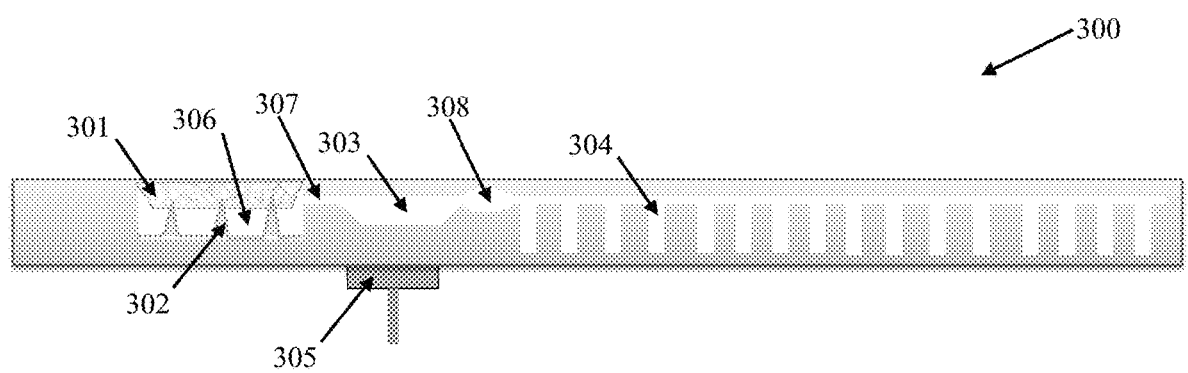
FIG. 3 illustrates a microfluidic testing cartridge according to one embodiment of the automated microbial detection system.

FIG. 3 illustrates a microfluidic testing cartridge 300 according to one embodiment of the automated microbial detection system. The microfluidic testing cartridge 300 includes a liquid cartridge 301 comprising a lysis buffer and cellular lysate. In some embodiments, the lysis buffer comprises phosphate buffer solution ("PBS"). In some embodiments, the buffer solution may also comprise a detergent (in addition to lysis) to enable efficient cellular wall and membrane disruption.

The microfluidic testing cartridge 300 also includes an impaling structure 302 embedded in a well 306 such that upon activation, the liquid cartridge 301 is punctured by the impaling structure 302 to allow release of the lysis buffer and cellular lysate into the well 306 and subsequent flow into the sample well 303 containing the charged particles through a flow channel 307. Puncturing of the liquid cartridge 301 by the impaling structure 302 may be enabled by an actor external to the microfluidic testing cartridge 300, such as a plunger driven by an actuator. In some embodiments, the impaling structure 302 may be driven by an internal self-actuating mechanism. As described above, the charged particles are collected in the sample well 303 by positioning the microfluidic testing cartridge 300 between the solid-state sampler and capture electrode 305 (i.e. FIG. 1). In an alternate embodiment, the liquid cartridge 301 is punctured by the impaling structure 302 and the lysis buffer and cellular lysate is simultaneously released into well 306 and sample well 303.

The charged particles in the sample well 303 are subsequently flown (i.e. pressure-driven) in the lysis buffer, such that the cellular lysate pools through mixing chamber 308. The mixing chamber 308 enables complete re-suspension of the charged particles in the lysis buffer solution to improve cellular lysis efficiency. The cellular lysate is then driven through a plurality of assay chambers 304 for segregating the cellular lysate. In one embodiment, prior to accepting the cellular lysate, each assay chamber 304 contains preexisting inactivated Phi29 rolling circle DNA polymerase, a genotype specific DNA oligomer primer for specific bacterial, archaeal, fungal or viral organisms, species, or taxa, and a fluorescent marker. The contents of each assay chamber 304 are activated upon contact with the lysis buffer/cellular lysate/charged particle mixture, and will be mixed with the lysed cells, cellular DNA, and cellular components. In one embodiment, the entire mixture or blend is then heated to about 30° C. using a Peltier device, though other directed, controlled heating mechanisms may be used which allow for isothermal amplification of targeted DNA from the blend. In one embodiment, the blend residence time in the assay chamber 304 varies in the range of between about 10 seconds and 1 hour. As the DNA amplifies, it binds with the fluorescence marker, which is detected using standard light based spectrophotometry. This allows for unique, taxon-specific identification and quantification in each assay chamber 304.

For example, a collection of lysed cells with genomic DNA, acquired from the charged particles, may contain bacteria A, bacteria B, archaea C, fungi D, fungi E, and virus F. In scenarios where multiple types microbes are present, segregation of the cellular lysate into the plurality of assay chambers 304 involves a separate assay chamber 304 for each individual bacteria, archaea, fungi, and virus (i.e. separate assay chambers for each of bacteria A, bacteria B, archaea C, fungi D, fungi E, and virus F). In one embodiment, the plurality of assay chambers 304 vary in size ranging from about 500 nL to about 10 μL. In one embodiment, each of the plurality of assay chambers 304 include between about 0.1 nanograms (ng) and 100,000 ng of genomic DNA, which will be amplified to between about 500 ng and 10 micrograms (μg) of specifically amplified genomic material for the individual bacteria, archaea, fungi, and virus of choice. All amplified and unamplified DNA will be labelled with a DNA-binding fluorescent marker for excitation and emission detection using standard protocols of light spectrophotometry.

Probe and Fluorescence Detection

In one embodiment, the fluorescence marker was prepared by molecular probe technology for highly multiplexed genotyping and involves hybridization of oligonucleotide probes to specific DNA sequences, enabling detection of genomes or genotypes. Molecular probes are roughly 20-200 base oligonucleotides, approximately 60 of which are unique to the selected genome of interest. Quantification of amplicons is performed by fluorescent DNA-binding dyes as described in other sections, or by counting circular DNA using nanoneedle biosensors that detect membrane impedance, or by any method that allows for quantification of DNA.

Array-synthesized oligonucleotides are an inexpensive source of large quantities of synthetic DNA; however, factors such as high synthesis error rates, uneven representation, and lack of access to individual oligonucleotides limit their use. One means for addressing these technological limitations is through Recombinase Directed Indexing (REDI). REDI involves integrating a complex library into yeast, site-specific recombination to index library DNA, and sequencing to identify sequence-perfect clones of interest. REDI may be used to generate a library of approximately 3,300 DNA probes exhibiting at least a 96% purity and unexpected uniformity. Alternatively, probes may be selected and synthesized for genome specific identification and oligonucleotides may be used to initiate rolling circle amplification.

In one embodiment, a nanoneedle biosensor technology is employed by placing a three-dimensional sensing array in each detection well, for real-time, sequence-specific detection of nucleic acids and is used together with the fluorescence marker (i.e. DNA probe) discussed above.

Structurally, the nanoneedle comprises two conductive layers separated by an insulator and a sensitive, nano-sized gap located at the nanoneedle tip. The nanoneedle tip is conjugated to oligonucleotides by surface functionalization, thereby allowing the capture and detection of sequences of interest. Samples are administered into a microfluidic channel providing access to the nanoneedles and changes in the molecules captured by the tip result in an immediate, measurable change in impedance across the sensing electrodes. Electrical detection offers an advantage over the currently available expensive and bulky equipment typically used for diagnostics in that it relies on far simpler instrumentation to enable lower costs, minimal sample manipulation, and a portable design. Impedance-based readouts are adaptable for performing real-time microbiome profiling experiments in clinical or field settings using a battery-operated, hand-held device. In one embodiment, the time for detection and analysis is less than 60 minutes. In a preferred embodiment, the time for detection and analysis is less than 30 minutes. In one embodiment, analytical specificity of the fluorescence detector is selected from one of at least 95% or 97% or 98% or 99% or 99.9% or 99.99%.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (i.e. "top," "bottom," "above," "below," "on," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed:

1. A method for automated microbial detection, comprising:
   collecting air particles into a solid-state sampler, the air particles including microbes;
   charging the air particles using a plasma field generated by propulsion electrodes;
   focusing the charged air particles toward a sample well of a microfluidic testing cartridge;
   tagging the charged air particles with a fluorescence marker;
   detecting a quantity of the microbes using a fluorescence detector.

2. The method of claim 1, further comprising:
   transmitting a signal of the fluorescence detector to a remote storage and analysis device;
   discarding the microfluidic testing cartridge; and
   loading an unused microfluidic testing cartridge.

3. The method of claim 1, wherein the microbes comprise at least one of bacteria, archaea, fungi, viruses, or a combination thereof.

4. The method of claim 1, wherein the solid-state sampler is an electro-kinetic ion focuser.

5. The method of claim 1, wherein the step of tagging the charged air particles comprises:
   puncturing a liquid cartridge comprising cell-lysis chemicals with an impaling structure embedded in the microfluidic testing cartridge releasing the cell-lysis chemicals;
   flowing the released cell-lysis chemicals into the sample well;
   mixing the flowed cell-lysis chemicals with the charged air particles, forming a blend;
   flowing the blend into a mixing chamber of the microfluidic testing cartridge to re-suspend the charged particles in the cell-lysis chemicals; and
   distributing the blend into at least one assay chamber of the microfluidic testing cartridge.

6. The method of claim 5, wherein the step of distributing the blend into at least one assay chamber comprises:
   activating pre-existing DNA polymerase, genotype-specific DNA oligomer primers, and fluorescent marker in each assay chamber;
   heating each assay chamber to enable isothermal DNA amplification; and
   binding the amplified DNA with the fluorescent marker.

7. The method of claim 6, wherein the DNA polymerase is a Phi29 rolling circle DNA polymerase.

8. The method of claim 5, wherein the cell-lysis chemicals comprise a lysis buffer, cellular lysate, and at least one detergent.

9. A method of tagging charged particles comprising:
   puncturing a liquid cartridge comprising cell-lysis chemicals with an impaling structure to release the cell-lysis chemicals;
   mixing the released cell-lysis chemicals with charged air particles including microbes to form a blend;
   contacting, in an assay chamber, the blend with a mixture preexisting in the assay chamber, the mixture comprising DNA polymerase, genotype-specific DNA oligomer primers, and fluorescent marker to form a system;
   heating the system to enable isothermal DNA amplification; and
   binding the amplified DNA with the fluorescent marker, wherein the charged particles are suspended in the cell-lysis chemicals.

10. The method of claim 9, wherein the DNA polymerase is a Phi29 rolling circle DNA polymerase.

11. The method of claim 9, wherein the cell-lysis chemicals comprise a lysis buffer, cellular lysate, and at least one detergent.

* * * * *